United States Patent [19]

Gunkel et al.

[11] Patent Number: 5,281,741
[45] Date of Patent: Jan. 25, 1994

[54] PROCESS FOR PREPARING ARYLDIPHOSPHATE ESTERS

[75] Inventors: Louis T. Gunkel, Yardley, Pa.; Henry J. Barda, North Brunswick, N.J.

[73] Assignee: FMC Corporation, Philadelphia, Pa.

[21] Appl. No.: 611,555

[22] Filed: Nov. 13, 1990

[51] Int. Cl.$^5$ .............................. C07F 9/09
[52] U.S. Cl. ...................... 558/92; 558/110
[58] Field of Search ...................... 558/92, 110

[56] References Cited

U.S. PATENT DOCUMENTS

| | | | |
|---|---|---|---|
| 2,058,394 | 10/1936 | Arvin | 260/2 |
| 2,520,090 | 8/1950 | Barrett | 260/461 |
| 3,159,533 | 12/1964 | Nelson | 167/30 |
| 3,169,925 | 2/1965 | Mahoney | 252/49.8 |
| 3,360,591 | 12/1967 | Giammaria | 260/930 |
| 3,422,453 | 1/1969 | Frank | 260/930 |
| 3,929,940 | 12/1975 | Mayerhoefer et al. | 260/930 |
| 3,987,008 | 10/1976 | Stackman | 260/45.95 D |
| 4,134,876 | 1/1979 | Horner et al. | 260/45.7 P |
| 4,150,068 | 4/1979 | Taniyama et al. | 260/930 |
| 4,203,888 | 5/1980 | Rashbrook | 260/45.7 P |
| 4,933,386 | 6/1990 | Nitoh et al. | 524/127 |

FOREIGN PATENT DOCUMENTS

| | | | |
|---|---|---|---|
| 58-170711 | 4/1985 | Japan | 558/92 |
| 63-227632 | 9/1988 | Japan | 558/110 |
| 734767 | 8/1955 | United Kingdom | 558/92 |

*Primary Examiner*—James H. Reamer
*Attorney, Agent, or Firm*—R. E. Elden; F. Ianno; R. L. Andersen

[57] ABSTRACT

A process is provided for preparing an aryl diphosphate ester containing less than 5% by weight of triarylphosphate. The process reacts a solution of a dihydroxy aromatic compound and an excess of phosphorus oxychloride in a nonaqueous solvent having a boiling point greater than 110° C. The excess phosphorus oxychloride and part of the solvent are distilled from the solution at atmospheric pressure and the intermediate, a diphosphotetrachloridate solution, is reacted with a monohydric aryl compound. After extracting with an aqueous, alkaline solution the product is recovered by distilling off the remaining solvent.

17 Claims, No Drawings

PROCESS FOR PREPARING ARYLDIPHOSPHATE ESTERS

The invention is a novel process for preparing aryldiphosphate esters with a low vapor pressure. Optionally, the viscosity of the aryldiphosphate ester is less than 250 centistokes at 37° C. (0.25 mm$^2$/s).

Triaryl phosphates are well known to be useful as flame retardants. However, they are too volatile for some applications. For example, triphenylphosphate has a vapor pressure of about 1.5 kPa at 245° C. Pure aryldiphosphate esters are known to have a very low vapor pressure. However, such compounds are very difficult to make with a low volatility without vacuum distillation in a wiped film still or the like to remove either excess phosphorus oxychloride or triaryl phosphates. For example, Japanese Kokai 63-227,632 teaches a process in which one mole of a dihydric aromatic, such as resorcinol and 1.5 moles phosphorus oxychloride are reacted at 80° to 100° C. After completion of the reaction the unreacted phosphorus oxychloride is removed by vacuum distillation and subsequently the intermediate is dissolved in a solvent and reacted with phenol or cresol to form a high molecular weight aryldiphosphate ester oligomer containing less than 1.5% by weight triaryl phosphate; the viscosity of the oligomer products ranges from about 3100 cps (3.1 Pas) to 89,000 centipoise (89 Pas) at 25° C. However, it has been found that when the mole ratio of dihydric aryl compound to phosphorus oxychloride is increased from 1:1.5 to 1:3 that the triaryl phosphate in the product increases to over 5% by weight.

British Patent No. 734,767 teaches the reaction of one mole of a dihydric aryl compound with two moles of phosphorus oxychloride and subsequently reacting the mixture with a hydroxy compound to form a viscous oil.

U.S. Pat. No. 4,134,876 discloses in one example reacting resorcinol and phosporus oxychloride in a mole ratio of 1:9 in the absence of a solvent, vacuum distilling the excess phosphorus oxychloride, reacting the residue with dimethylphenol and again vacuum distilling to produce a product containing some dimer.

The present invention overcomes the problems of the prior art by providing a process which produces an aryl diphosphate product containing less than 5% by weight triaryl phosphate without the need to remove phosphorus oxychloride by vacuum distillation. The process comprises the steps of:

a. incorporating phosphorus oxychloride, a catalytic quantity of a Friedel-Crafts catalyst and sufficient dihydric aryl compound into an inert nonaqueous solvent to provide a first reaction mixture having a mole ratio of at least 3 moles of phosphorus oxychloride per mole of dihydric aryl compound, said solvent having a boiling point of at least 110° C. at one atmosphere;

b. heating the first reaction mixture at substantially one atmosphere for a time and temperature sufficient to evolve hydrogen chloride therefrom and to convert substantially all of the dihydric aryl compound into the corresponding diphosphorotetrachloridate;

c. distilling part of the solvent from said first reaction mixture at substantially one atmosphere for a sufficient time to substantially remove unreacted phosphorus oxychloride;

d. incorporating about four moles of a monohydric aryl compound into the first reaction mixture per mole of diphosphorotetrachloridate therein, thereby forming a second reaction mixture;

e. heating said second reaction mixture in the presence of a catalytic quantity of a Friedel-Crafts catalyst at substantially one atmosphere and at a temperature sufficient to evolve hydrogen chloride therefrom and sufficient to convert substantially all of the diphosphorotetrachloridate in the second reaction mixture into the corresponding aryldiphosphate ester;

f. extracting unreacted monohydric aryl compound from the second reaction mixture from step (e) by contacting said second reaction mixture with an aqueous, alkaline solution, g. separating the aqueous, alkaline solution from the second reaction mixture, and h. evaporating solvent from the second reaction mixture from step (g) to provide an aryl diphosphate ester containing less than 5% by weight triaryl phosphate.

It is critical to remove any free phosphorus oxychloride (POCl$_3$) from the first reaction mixture before adding a monohydric aryl compound, to minimize production of triaryl phosphate. Unexpectedly, it was found that when an excess of phosphorus oxychloride was employed (more than two moles per mole of dihydric aryl compound) in the first reaction mixture that vacuum stripping was ineffective in reducing the triaryl phosphate content of the final product to less than 5% by weight.

It was found that an aryldiphosphate product could be produced containing less than 5% by weight triaryl phosphate by incorporating a solvent with a boiling point greater than that of phosphorus oxychloride, and distilling the first reaction mixture after completion of the reaction of the dihydric aryl compound. This eliminates the prior art's need for complex vacuum stripping equipment such as a wiped film evaporator.

Any solvent may be employed which is nonreactive with the starting materials, the intermediate product or the final product. Alcohols, for instance, would react with the POCl$_3$ or transesterify with the product. Acetates can also hydrolize and transesterify with the product. The boiling point desirably should be at least 10° C. above the boiling point of POCl$_3$ (107.2° C.) to eliminate the need for a distillation column with many plates, although that could be done. It is preferred to employ a solvent with a boiling point of 130° to 145° C., about 20° to 35° C. higher than that of POCl$_3$ allowing the separation of the two compounds to be accomplished with a simple packed column with only several theoretical plates.

Suitable solvents include aliphatic hydrocarbons such as octane, nonane and decane; aromatic hydrocarbons such as xylene, mesitylene, pseudocumene, ethylbenzene, ethyltoluene, propylbenzene, and durene; ethers, such as dibutyl ether and cellosolves; and halogenated compounds, such as trichloroethane, chlorobenzene and the like.

Aromatic solvents are particularly desirable, such as xylene. Ethers are also desirable. Dibutyl ether has a similar boiling point to xylene (142.4° C.) but has an additional advantage in that both resorcinol and phenol are soluble in it. This is important in large scale processes where adding resorcinol (mp 108° C.) as a solid presents an engineering problem. Dissolving the dihydric aryl compound in a solvent makes the addition easier.

Any dihydric aryl compound may be incorporated into the first reaction mixture.

Suitable dihydric aryl compounds include resorcinol, hydroquinone, bisphenols such as bisphenol A, bisphenolsulfone, bisphenol methanes, biphenols as well as the substituted dihydric aryl compounds. Desirably, the dihydric aryl compound will be resorcinol or hydroquinone when the goal is to provide a product with the highest phosphorus content. If a liquid aryldiphosphate is desired rather than a solid, a nonsymmetric dihydric aryl compound should be employed, such as resorcinol.

The present process is particularly effective for manufacturing a low viscosity liquid aryl diphosphate composition. A ratio of one mole of a dihydroxyaryl compound to at least three moles of phosphorus oxychloride (1:3) is desirable. A mole ratio of at least 1:5 is critical when a product is desired with a viscosity of less than about 300 cps (0.3 Pas) at 25° C. It is generally unnecessary and is uneconomical to employ a mole ratio of greater than 1:7.

An unexpected advantage of the present process is that the presence of the solvent in the second reaction mixture makes it easier to separate the reaction mixture from the alkaline, aqueous wash solution. Another unexpected advantage is that the solvent reduces the danger of overheating in the event an excess of a hydroxy compound is incorporated into the reaction mixture.

Any alkali which is strong enough to form a salt with the monohydric aryl compound can be employed in the alkaline, aqueous solution, desirably either sodium hydroxide or potassium hydroxide. Generally it is desirable to wash the second reaction mixture with water following the extraction with the alkaline, aqueous solution.

Following separation of the second reaction mixture from the alkaline, aqueous solution and/or wash water the solvent is removed by evaporation. Although this may be done at atmospheric pressure it is generally desirable to employ subatmospheric pressure for this one operation.

The oligomer content of the product generally can be controlled by varying the ratio of dihydric phenol and phosphorus oxychloride in the first reaction mixture. One skilled in the art will also recognize that incorporating a dihydric aryl compound into the second reaction mixture will also increase the oligomer content and hence, the viscosity, in the final product. Generally, a product with an oligomer content of about 25% or less results in a product with a low kinematic viscosity, that is a viscosity of less than 250 centistokes at 37° C. A product with a viscosity of up to 3000 centistokes may be desirable for some applications.

The best mode of practicing the invention will be evident to one skilled in the art from the above disclosure and from the following nonlimiting examples.

EXAMPLE A

Non-Solvent Run

Fifteen hundred twenty grams (10 moles) of $POCl_3$, 165 grams of resorcinol (1.375 moles), and 4 grams of magnesium chloride were charged into a flask equipped with stirrer, heating mantle, temperature controller, and a reflex condenser which vented to a caustic scrubber. The flask contents were heated to 120° C. over a three hour period. Reaction was followed by measuring HCl evolution which was trapped in the caustic scrubber. When the HCl evolution stopped, the pot contents were then stripped of $POCl_3$ in a rotary evaporator at 90° C. and 5 mm Hg vacuum. The pot contents at this point weighed 467.6 grams. To this material were added 676.9 grams of phenol and 2.0 grams of $MgCl_2$. The mixture was heated to 120° C. for one hour and then raised to 160° C. after the HCl evolution ceased. The crude reaction mixture was run through a wiped film still to remove excess phenol. The phenol content was lowered to 0.3 percent by this procedure. The final product weighed 392 grams, had a triphenyl phosphate content of 9.9 percent, a diphenyl hydroxyphenyl phosphate content of 1.4 percent, the remainder being the product, tetraphenyl resorcinol diphosphate and oligomers.

EXAMPLE B

Non-Solvent Run

Six hundred grams of $POCl_3$ (3.93 moles) and 0.2 grams of magnesium chloride were charged to a flask equipped as in Example A. The mixture was heated to 90° C. and 110 grams of resorcinol were added (1.0 moles). The reaction temperature was raised to 113° C. The reaction was continued until 57 grams of HCl had evolved from the reaction.

The excess $POCl_3$ was then stripped out of the flask using reduced pressure. A total of 224.4 grams of $POCl_3$ were removed.

Three hundred and seventy grams of phenol and 0.25 grams of magnesium chloride were then added to the reaction mixture which was heated to 150° C. until the HCl evolution ceased. The excess phenol was then stripped off using reduced pressure (0.2 mm and 75° C.). Seventy nine grams of phenol were recovered. The stripped product weighed 398 grams. The triphenyl phosphate concentration in this material was 8.72 percent.

EXAMPLE 1

Xylene Solvent Run

Two hundred eighty grams of $POCl_3$ (1.82 moles), 300 grams of xylene and 0.5 grams of aluminum chloride were charged to a flask equipped as in Example A. The mixture was heated to 113° C. and 40 grams (0.363 moles) of resorcinol were added. Over a two hour period, 26.1 grams (0.71 moles) of HCl were trapped in the caustic scrubber.

At the end of the HCl evolution, the pot was heated to the boiling point and the $POCl_3$ was distilled over and "chased" out by the xylene solvent. The distillation was continued until the overhead temperature reached 142° C.

One hundred grams of phenol (1.30 moles) were added to the pot and heated for two hours at 150° C. Forty grams of HCl were collected from this stage of the reaction. The pot contents were then washed twice with 300 ml portions of a five percent solution of sodium hydroxide in water. This was followed by a 300 ml water wash. The washed material was then vacuum stripped to remove xylene and water. The dried product weighed 166.2 grams. HPLC analysis showed 1.7 percent triphenyl phosphate, 0.4 percent diphenyl hydroxy phenyl phosphate and 97.4 tetraphenyl resorcinol diphosphate and oligomers.

EXAMPLE 2

Xylene Solvent Run

Four hundred six grams of $POC_3$ (2.65 moles), 400 grams of xylene and 0.8 grams of aluminum chloride were charged to a one liter flask equipped as in Example A. The mixture was heated to 113° C. and 60 grms (0.545 moles) of resorcinol were added. Over a two hour period, 41.0 grams (1.12 moles) of HCl gas were trapped in the caustic scrubber.

At the end of the HCl evolution, 200 ml of xylene were added to the pot which was then heated and the $POCl_3$ was distilled at atmospheric pressure over and chased out by the xylene solvent. The distillation was continued until the overhead temperature reached 142° C. The pot temperature reached 150° C. at the end. GC analysis indicated the pot contents to be free of $POCl_3$.

One hundred eighty-five grams of phenol (1.96 moles) were then added to the pot which was heated for two hours at 150° C. Sixty six grams of HCl were collected. GC analysis of the pot contents after the phenol reaction showed 1.5 percent of phenol remaining in the mixture. The pot contents were then washed twice with 300 ml portions of a five percent solution of sodium hydroxide in water to remove the excess phenol. This was followed by a 300 ml water wash. The washed material was then vacuum stripped to remove xylene and water. The dried product weighed 246.0 grams. HPLC analysis showed 1.87 percent triphenyl phosphate, 0.1 percent diphenyl hydroxy phenyl phosphate and 97.7 tetraphenyl resorcinol diphosphate and oligomers.

EXAMPLE 3

Xylene Solvent Run

Seven hundred grams of $POCl_3$ (4.56 moles), 300 grams of xylene and 1.0 grams of aluminum chloride were charged to a one liter flask equipped as in Example A. This mixture was heated to 113° C. and 100 grams (0.90 moles) of resorcinol were added. Over a two hour period, 68.5 grams (1.88 moles) of HCl gas was trapped in a caustic scrubber.

At the end of the HCl evolution, 200 ml of xylene were added to the pot which was then heated and the excess $POCl_3$ was distilled over and chased out by the xylene solvent. The distillation was continued until the overhead temperature reached 142° C.

Two hundred ninety-eight grams of phenol (3.16 moles) were then added to thee pot and heated for two hours at 150° C.; one hundred eleven grams of HCl were collected. GC analysis of the reaction mixture showed 0.8 percent phenol remaining after the reaction. The pot contents were then washed twice with 750 ml portions of a two percent solution of sodium hydroxide in water. This was followed by a 700 ml water wash. The washed material was then vacuum stripped to remove xylene and water. The dried product weighed 431.0 grams. HPLC analysis showed 1.37 percent triphenyl phosphate, 0.16 percent diphenyl hydroxy phenyl phosphate and 98.3 percent tetraphenyl resorcinol diphosphate and oligomers.

EXAMPLE 4

Dibutyl Ether Solvent Run

Two hundred eighty grams of $POCl_3$ (1.82 moles), 200 grams of dibutyl ether and 0.5 grams of aluminum chloride were charged to a flask equipped as in Example A. The mixture was heated to 113° C. and 40 grams (0.363 moles) of resorcinol dissolved in 100 grams of dibutyl ether were added over an hour. After a two hour period, 26.6 grams (0.72 moles) of HCl gas was trapped in a caustic scrubber.

At the end of the HCl evolution, the pot was heated and the $POCl_3$ was distilled over and chased out by the butyl ether solvent. The distillation was continued until the overhead temperature reached 142° C. GC analysis of the pot contents indicated that it was free from $POCl_3$.

One hundred twenty-three grams of phenol (1.30 moles) dissolved in 100 ml of dibutyl ether were then added to the pot and heated for two hours at 150° C. Forty-eight grams of HCl was collected from this stage of the reaction. The pot contents were then washed twice with 300 ml portions of a three percent solution of sodium hydroxide in water. This was followed by a 300 ml water wash. The washed material was then vacuum stripped to remove butyl ether and water. The dried product weighed 123.3 grams. HPLC analysis showed 1.86 percent triphenyl phosphate, 0.15 percent diphenyl hydroxy phenyl phosphate and 97.4 tetraphenyl resorcinol diphosphate and oligomers.

EXAMPLE 5

Xylene Solvent Run

Twenty-eight hundred grams of $POCl_3$ (18.2 moles), 1000 grams of xylene and 4.0 grms of aluminum chloride catalyst were charged to a flask equipped as in Example A. The pot was heated to 110° C. and resorcinol was added in 50 gram portions every 15 minutes until 400 grams total had been charged. The temperature was held for 4 hours at which time 274 grams of HCl had been collected.

The reflux condenser was replaced with a six inch glass packed column. Five hundred ml of xylene were added to the flask and the excess $POCl_3$ was distilled out and chased with some solvent. The distillation was continued until the overhead temperature reached 140° C. A gas chromatograph analysis of the pot indicated the $POCl_3$ level was undetectable.

Eleven hundred sixty grams of phenol and six grams of aluminum chloride were added to the pot in four equal increments over two hours at 140° C. Four hundred thirty-eight grams of HCl were collected from the reaction. The phenol content of the reaction mixture at this point was 0.78 percent.

The phenol was washed out with 1200 grms of a saturated salt solution containing 3 percent sodium hydroxide. This was followed by two water washes of the same volume. The reaction mixture was then stripped under vacuum to remove solvent and water. The weight of the dried liquid product was 1932 grams. Analysis of the material by HPLC showed 1.1 percent triphenyl phosphate, 0.28 percent diphenyl hydroxyphenyl phosphate and 98.49 percent tetraphenyl resorcinol diphosphate and oligomers.

EXAMPLE 6

Large Scale Xylene Solvent Run

A first reaction mixture consisting of 1006 pounds of xylene, 500 grams of anhydrous aluminum chloride, and 999 pounds of phosphorus oxychloride were charged under a nitrogen pad into a 500 gallon glass lined reactor.

This mixture was heated to 95° C. One hundred forty pounds of resorcinol melted in 54 pounds of xylene were added to the reactor over a two hour period. The HCl off-gas was collected in a caustic scrubber. The reaction was followed by the disappearance of resorcinol via GC analysis. Following the $POCl_3$/resorcinol reaction, the excess $POCl_3$ was stripped from the reactor and chased with xylene until the distillate was essentially xylene. The xylene distilled off was replaced with fresh material to maintain the volume.

In the second step, an additional 500 grams of aluminum chloride was added to the reactor and the temperature was controlled at 120° C. At this point 430 pounds of phenol were melted into a charge tank and fed into the reactor over a two hour period, the HCl off-gas being collected in a caustic scrubber. The reaction temperature was maintained at 140° C. until the reaction was complete as evidenced by GC analysis indicating the phenol concenrration to be constant at about 0.8 percent in the mixture. The xylene/product solution was then washed with 1000 pounds of a 3 percent NaOH solution at 30° C. for one hour and then allowed to separate. The aqueous and xylene solutions separated quickly and analysis of the organic phase showed no phenol present. The organic phase was then given two 1000 pound water washes, which also separated easily.

Following the water washes, the xylene was stripped off, first at atmospheric pressure and finally under 200 mm Hg. vacuum and a maximum temperature of 140° C. until the xylene was removed.

The stripped product was a clear solution which weighed 639 pounds. This corresponds to a 96 percent yield based on resorcinol. The physical properties of the product are shown in Table I.

TABLE I

ANALYSIS OF 55 GALLON TETRAPHENYL RESORCINOLDIPHOSPHATE SAMPLE

| Property | Value |
|---|---|
| % Phosphorus | 10.83% |
| Color | 500 APHA |
| % Water | 0.06% |
| Acidity | 0.06 mg KOH/gm |
| Viscosity | 149 cts @ 100° F. |
| | 11.8 cts @ 210° F. |
| Specific Gravity | 1.29 @ 25° C. |
| Odor | Slight |
| RDP* | 70.68% |
| Oligomers | 27.36% |
| Triphenyl Phosphate | 1.96% |

*tetraphenyl resorcinoldiphosphate

We claim:

1. A process for manufacturing an aryldiphosphate ester composition comprising the steps of:
   a. incorporating phosphorus oxychloride, a catalytic quantity of a Friedel-Crafts catalyst and sufficient dihydric aryl compound into an inert non-aqueous solvent to provide a first reaction mixture having a mole ratio of at least 3 moles of phosphorus oxychloride per mole of dihydric aryl compound, said solvent having a boiling point of at least 110° C. at one atmosphere;
   b. heating the first reaction mixture at substantially one atmosphere for a time and temperature sufficient to evolve hydrogen chloride therefrom and to convert substantially all of the dihydric aryl compound into the corresponding diphosphorotetrachloridate;
   c. distilling part of the solvent from said first reaction mixture at substantially one atmosphere for a sufficient time to substantially remove unreacted phosphorus oxychloride;
   d. incorporating about four moles of a monohydric aryl compound into the first reaction mixture per mole of diphosphorotetrachloridate therein, thereby forming a second reaction mixture;
   e. heating said second reaction mixture in the presence of a catalytic quantity of a Friedel-Crafts catalyst at substantially one atmosphere and at a temperature sufficient to evolve hydrogen chloride therefrom and sufficient to convert substantially all of the diphosphorotetrachloridate in the second reaction mixture into the corresponding aryldiphosphate ester;
   f. extracting unreacted monohydric aryl compound from the second reaction mixture from step (e) by contacting said second reaction mixture with an aqueous, alkaline solution,
   g. separating the aqueous, alkaline solution from the second reaction mixture, and
   h. evaporating solvent from the second reaction mixture from step (g) to provide an aryl diphosphate ester containing less than 5% by weight triaryl phosphate.

2. The process of claim 1 wherein the viscosity of the aryl diphosphate ester product is less than 3 mm$^2$/s at 25° C.

3. The process of claim 1 wherein sufficient dihydric aryl compound is incorporated in step (a) to provide a mole ratio of 5 moles of phosphorus oxychloride per mole of dihydric aryl compound and to provide a product with a viscosity of less than 0.25 mm$^2$/s at 25° C.

4. The process of claim 1 wherein the solvent has a boiling point of 130° to 145° C.

5. The process of claim 2 wherein the solvent has a boiling point of 130° to 145° C.

6. The process of claim 3 wherein the solvent has a boiling point of 130° to 145° C.

7. The process of claim 4 wherein the solvent has a boiling point of 130° to 145° C.

8. The process of claim 1 wherein the solvent is selected from the group consisting of xylene and dibutyl ether.

9. The process of claim 2 wherein the solvent is selected from the group consisting of xylene and dibutyl ether.

10. The process of claim 3 wherein the solvent is selected from the group consisting of xylene and dibutyl ether.

11. The process of claim 4 wherein the solvent is selected from the group consisting of xylene and dibutyl ether.

12. A process for manufacturing an aryldiphosphate ester comprising the steps of;
   a. incorporating phosphorus oxychloride, a catalytic quantity of a Friedel-Crafts catalyst and sufficient dihydric aryl compound into a nonaqueous inert solvent to provide a first reaction mixture having a mole ratio of at least 5 moles of phosphorus oxychloride per mole of dihydric aryl compound, said solvent having a boiling point of at least 110° C. at one atmosphere;
   b. heating the first reaction mixture at substantially one atmosphere for a time and temperature sufficient to evolve hydrogen chloride therefrom and to convert substantially all of the dihydric aryl compound into the corresponding diphosphorotetrachloridate;
   c. distilling solvent from said first reaction mixture at its boiling point for a sufficient time to substantially remove unreacted phosphorus oxychloride;
   d. incorporating about four moles of a monohydric aryl compound into the first reaction mixture per mole of diphosphorotetrachloridate therein, thereby forming a second reaction mixture;
   e. heating said second reaction mixture in the presence of a catalytic quantity of a Friedel-Crafts catalyst at substantially one atmosphere and at a temperature sufficient to evolve hydrogen chloride therefrom and to convert substantially all of the diphosphorotetrachloridate in the second reaction mixture into the corresponding aryldiphosphate ester;

f. extracting unreacted monohydric aryl compound from the second reaction mixture from step (e) by contacting said second reaction mixture with an aqueous, alkaline solution;

g. separating the aqueous, alkaline solution from the second reaction mixture, and h. evaporating solvent from the second reaction mixture to provide an aryl diphosphate ester having a viscosity of less than 25 mm$^2$/s (250 centistokes at 37° C. and containing less than 5% by weight triaryl phosphate.

13. A process for manufacturing an aryldiphosphate ester composition comprising the steps of:

a. incorporating phosphorus oxychloride, a catalytic quantity of a Friedel-Crafts catalyst and sufficient dihydric aryl compound selected from the group consisting of substituted and unsubstituted resorcinol, hydroquinone, bisphenol, bisphenolsulfone, bisphenol methane and biphenol, into an inert non-aqueous solvent to provide a first reaction mixture having a mole ratio of at least 3 moles of phosphorus oxychloride per mole of dihydric aryl compound, said solvent selected from the group consisting of octane, nonane, decane, xylene, mesitylene, pseudocumene, ethylbenzene, ethyltoluene, propylbenzene, durene, dibutylether, cellosolve, trichloroethane and chlorobenzene;

b. heating the first reaction mixture at substantially one atmosphere for a time and temperature sufficient to evolve hydrogen chloride therefrom and to convert substantially all of the dihydric aryl compound into the corresponding diphosphorotetrachloridate;

c. distilling part of the solvent from said first reaction mixture at substantially one atmosphere for a sufficient time to substantially remove unreacted phosphorus oxychloride;

d. incorporating about four moles of a monohydric aryl compound, into the first reaction mixture per mole of diphosphorotetrachloridate therein, thereby forming a second reaction mixture;

e. heating said second reaction mixture in the presence of a catalytic quantity of a Friedel-Crafts catalyst at substantially one atmosphere and at a temperature sufficient to evolve hydrogen chloride therefrom and sufficient to convert substantially all of the diphosphorotetrachloridate in the second reaction mixture into the corresponding aryldiphosphate ester;

f. extracting unreacted monohydric aryl compound from the second reaction mixture from step (e) by contacting said second reaction mixture with an aqueous, alkaline solution, g. separating the aqueous, alkaline solution from the second reaction mixture, and h. evaporating solvent from the second reaction mixture from step (g) to provide an aryl diphosphate ester containing less than 5% by weight triaryl phosphate.

14. The process of claim 13 wherein the viscosity of the aryl diphosphate ester product is less than 3 mm$^2$/s at 25° C.

15. The process of claim 13 wherein sufficient dihydric aryl compound is incorporated in step (a) to provide a mole ratio of 5 moles of phosphorus oxychloride per mole of dihydric aryl compound and to provide a product with a viscosity of less than 0.25 mm$^2$/s.

16. The process of claim 13 wherein the solvent is selected from the group consisting of xylene and dibutyl ether.

17. The process of claim 13 wherein the dihydric aryl compound is resorcinol.

* * * * *

UNITED STATES PATENT AND TRADEMARK OFFICE
CERTIFICATE OF CORRECTION

PATENT NO. : 5,281,741

DATED : January 25, 1994

INVENTOR(S) : Louis T. Gunkel and Henry J. Barda

It is certified that error appears in the above—identified patent and that said Letters Patent is hereby corrected as shown below:

Column 6, lines 63-64, "disappearance of resoroinol via GC analysis." should read --disappearance of resorcinol via GC analysis.--.
Column 9, line 15, "25 mm$^2$/s (250 centistokes at" should read --2.5 mm$^2$/s (250 centistokes) at--.

Signed and Sealed this

Twenty-eighth Day of June, 1994

Attest:

BRUCE LEHMAN

*Attesting Officer*     *Commissioner of Patents and Trademarks*